United States Patent [19]

Kawarabayashi et al.

[11] Patent Number: 5,090,156

[45] Date of Patent: Feb. 25, 1992

[54] METHOD FOR STORING BULBS

[75] Inventors: Waichirou Kawarabayashi; Yumi Ishii; Shigeru Takahashi, all of Yamaguchi, Japan

[73] Assignee: Mitsui Petrochemical Industries Ltd., Tokyo, Japan

[21] Appl. No.: 671,162

[22] Filed: Mar. 14, 1991

Related U.S. Application Data

[63] Continuation of Ser. No. 555,797, Jul. 23, 1990, abandoned, and Ser. No. 301,420, Jan. 25, 1989, abandoned.

[30] Foreign Application Priority Data

| Feb. 3, 1988 | [JP] | Japan | 63-21900 |
| Feb. 4, 1988 | [JP] | Japan | 63-22776 |

[51] Int. Cl.$^5$ ............................................. A01G 7/06
[52] U.S. Cl. .................................................. 47/58
[58] Field of Search ....................................... 47/58

[56] References Cited

U.S. PATENT DOCUMENTS

| 1,789,068 | 1/1931 | Colle et al. | 47/18 |
| 3,146,548 | 9/1964 | Van Waveren | 47/58 |
| 3,314,194 | 4/1967 | Halleck | 47/84 |
| 3,443,928 | 5/1969 | Batchelor | 71/78 |
| 4,118,890 | 10/1978 | Shore | 47/84 |
| 4,124,369 | 11/1978 | Kramer et al. | 71/77 |
| 4,227,913 | 10/1980 | Kupleian | 71/78 |
| 4,337,080 | 6/1982 | Szkrybalo | 71/78 |
| 4,341,551 | 7/1982 | Kruger | 71/78 |
| 4,777,762 | 10/1988 | Redenbaugh et al. | 47/DIG. 9 |

FOREIGN PATENT DOCUMENTS

| 1273249 | 7/1968 | Fed. Rep. of Germany | 47/57.6 |
| 2259514 | 11/1987 | Japan | 47/69 |
| 692590 | 10/1979 | U.S.S.R. | 47/DIG. 9 |

OTHER PUBLICATIONS

Nitzsche, W., (1980) "One Year Storage of Dried Carrot Callus" Z. Pflanzenphysiol. Bd. vol. 100, S. pp. 269-271.

Kitto, S. L. et al., (1985) "Hardening Treatments Increase Survival of Synthetically-Coated Asexual Embryos of Carrot" J. Amer. Soc. Hort. Sci. vol. 110, No. 2, pp. 283-286.

Gray, D. J., (1987) "Quiescence in Monocotyledonous and Dicotyledonous Somatic Embryos Induced by Dehydration" HortScience, vol. 22, No. 5, pp. 810-814.

Weaver, R. J. (1972) Plant Growth Substances in Agriculture (Pub.) W. H. Freeman and Co., San Francisco, pp. 18-20, 104-109, 130-133, 151-157, 170-175, 312-319, 394-398 and 402-406.

Primary Examiner—James R. Feyrer
Attorney, Agent, or Firm—Nixon & Vanderhye

[57] ABSTRACT

A method for storing a seedling, a nursery plant and a bulb for a long period under an ordinary temperature condition by immersing a seedling, a nursery plant and a bulb in a solution containing a growth inhibitor or an osmoregulator, sealing thus treated seedling, nursery plant and bulb in a suitable container and then preserving the sealed seedling, nursery plant and bulb at an ordinary temperature.

8 Claims, No Drawings ions Ser. No. 07/301,420, filed Jan. 25, 1989, abandoned and Ser. No. 07/555,797, filed July 23, 1990, now abandoned.

BACKGROUND OF THE INVENTION

This invention relates to a method for storing a seedling, a nursery plant and a bulb. More specifically, this invention relates to a method for storing a seedling, a nursery plant and a bulb immersed in a prescribed solution over a long period in a prescribed container.

In order to produce a cut flower, a potted flower and the like year-roundly, the cultivation of a seedling, a nursery plant and a bulb thereof as materials at periods other than a period suitable for the cultivation thereof has been so far carried out. In this case, it is required to store the seedling, the nursery plant and the bulb for the cultivation period. When the storage extends over a long period, the respiratory consumption is high and the growth of a plant body is initiated to cause germination and rooting. In order to control the oxygen respiration, the germination and the rooting as above, the storage is required to be carried out under a low temperature condition or by controlling the oxygen concentration. For these purposes, storage using a refrigerator, a cooler and the like and CA storage are carried out. However, these storing methods require a sizable expenditure on equipment, electricity and the like. In such circumstances, such storage methods are employed not in the stages of a common retailer and a common consumer but solely in the stage of a producer.

SUMMARY OF THE INVENTION

Based on the recognition that the conventionally known methods for storing a seedling, a nursery plant and a bulb have the foregoing various problems, the present inventors have made a study of a method capable of dissolving the problems, making the storage of these plant bodies at an ordinary temperature possible to thus enable to reduce the expenditure in comparison with the conventional methods and being readily usable in the stages of a common retailer and a common consumer.

As the result, they have found that the foregoing purpose can be attained by adopting the following method to complete the present invention.

That is, the gist of the present invention lies in the provision of a method for storing a seedling, a nursery plant and a bulb characterized by immersing a seedling, a nursery plant and a bulb of a plant in a solution containing a growth inhibitor or an osmoregulator, sealing thus treated seedling, nursery plant and bulb in a prescribed container together with a suitable moisture retainer and then storing the sealed seedling, nursery plant and bulb at an ordinary temperature.

According to the present method, a seedling, a nursery plant and a bulb of a plant can be stored even at an ordinary temperature to sharply reduce expenditures for storing, as compared with the conventional storing methods by which not only the freshness of a seedling, a nursery plant and a bulb is forced to be maintained under a low temperature condition over a long period but also the initiation of growth is uncontrollable. In addition, the present invention makes the storage under an ordinary temperature condition possible, so that a seedling, a nursery plant and a bulb can be easily stored at a retail store or a common consumer's house over a long period to bring about the possibility that the distribution system of a seedling, a nursery plant and a bulb may be innovated into more flexible one.

DETAILED DESCRIPTION OF THE INVENTION

As previously noted, the present invention provides a method for storing a seedling, a nursery plant and a bulb over a long period under an ordinary temperature condition by immersing the seedling, the nursery plant and the bulb in a solution containing a growth inhibitor or an osmoregulator, sealing thus treated seedling, nursery plant and bulb in a container together with a suitable moisture retainer and then preserving the sealed seedling, nursery plant and bulb under an ordinary temperature condition.

As a growth inhibitor to be used in the present storage method by dissolving in an immersing solution, a conventionally known plant growth inhibitor can be used. As specific examples thereof, dormant hormones such as abscisic acid, etc. and elongation retardants such as CCC, B-nine, ancymidol, etc. can be enumerated.

As an osmoregulator to be used in the present method by dissolving in an immersing solution, a conventionally known osmoregulator can be used. As specific examples of the osmoregulator, sucrose, glucose, fructose, mannose, sorbitol, mannitol, etc. can be enumerated.

A plant to which the present method can be applied is not restricted particularly, so that any of plants to which the low temperature storage has been so far applied can be stored by using the present method. In the present invention, a white trumpet lily, a speciosum lily, a Thunberg lily, a tulip, a gladiolus, a bulbous iris, a carnation, a gypsophilla, etc. can be exemplified as the plant. Incidentally, these plants can include small plant bodies thereof proliferated by the tissue culture other than those obtained by usual open cultivation.

As a container to be used in the present invention for sealing a plant body therein, any container having oxygen permeability and capability of maintaining humidity properly will do. As examples of the container, polypropylene bag and the like can be enumerated in the present invention.

As a moisture retainer to be used in the present invention, the conventionally known materials such as bog moss, sawdust, vermiculite, etc. can be employed.

As a method for immersing a seedling, a nursery plant and a bulb in a solution containing a growth inhibitor to be conducted in the present invention, a method in which the whole plant body is immersed in a solution containing the above growth inhibitor for a period of 1 hour to 1 week, preferably of 24 hours to 3 days and nights can be exemplified.

In the present invention, a growth inhibitor is made to have a concentration ranging from 1 to 1,000 mg/l, preferably 10 to 100 mg/l. In case of the concentration being high, the growth after the takeout of a plant body from a container is often inhibited, so that it is preferred that the concentration is selected from the above range.

As a method for immersing a seedling, a nursery plant and a bulb in a solution containing an osmoregulator to be conducted in the present invention, a method in which the whole plant body is immersed in a solution containing the above osmoregulator for a period of 1 hour to 1 week, preferably of 24 hours to 3 days and nights can be exemplified. In the present invention, the concentration of an osmoregulator is adjusted to be in the range of 5 to 10 atm.

EXAMPLE

Hereinafter, the present invention will be described more specifically, referring to examples.

EXAMPLE 1

5~7 mm diam. white trumpet lily bulbs proliferated by tissue culture were immersed in a solution containing 20 mg/l abscisic acid for 24 hours and then washed with running water. Thus treated bulbs were respectively embedded in vermiculite containing moisture properly, sealed in polypropylene bags and then stored at an ordinary temperature (24°~26° C.) for 3 months. As controls, bulbs immersed in distilled water for 24 hours were used.

After 3 months, the ratio of bulbs having leaves elongated to a length of 0.5 cm or more was examined. As the result, it was found that the leaf emergence ratio of bulbs immersed in an abscisic acid solution was 0%, whereas that of bulbs immersed in distilled water was 100% because the growth initiation could not be controlled.

Incidentally, bulbs whose growth initiation was controlled by immersing in an abscisic acid solution and then storing at an ordinary temperature were planted in pots and then grown in a greenhouse regulated to 23° C. As the result, leaves emerged from the bulbs and grew normally and flowered after 5 months.

EXAMPLE 2

The procedure was repeated in the same manner as in Example 1, except that a solution containing 20 mg/l CCC [(2-chloroethyl)trimethylammonium chloride] instead of abscisic acid as a plant growth inhibitor was used and the storage period was set to 2 months.

As a result of examining the ratio of bulbs having leaves elongated to a length of 0.5 cm or more, the leaf emergence ratio of bulbs immersed in a CCC solution was 50%, whereas that of bulbs immersed in distilled water was 87.5%.

EXAMPLE 3

5~7 mm diam. white trumpet lily bulbs prolifelated by tissue culture were immersed in a solution containing 10 atm. sucrose for 24 hours and then washed with running water. These bulbs were respectively embedded in vermiculite containing moisture properly, sealed in polypropylene bags and then stored at an ordinary temperature (24°~26° C.) for 2 months. As controls, bulbs immersed in distilled water for 24 hours were used.

After 2 months, the ratio of bulbs having leaves elongated to a length of 0.5 cm or more was examined. As the result, the leaf emergence ratio of bulbs immersed in a solution containing 10 atm. sucrose was 20%, whereas that of bulbs immersed in distilled water was 87.5%.

EXAMPLE 4

5~7 mm diam. white trumpet lily bulbs proliferated by tissue culture were immersed in a solution containing 10 atm. sorbitol for 24 hours and then washed with running water. These bulbs were respectively embedded in vermiculite containing moisture properly, sealed in polypropylene bags and then stored at an ordinary temperature (24°~26° C.) for 2 months. As controls, bulbs immersed in distilled water for 24 hours were used.

After 2 months, the ratio of bulbs having leaves elongated to a lenght of 0.5 cm or more was examined. As the result, the leaf emergence ratio of bulbs immersed in a solution containing 10 atm. sorbitol was 33.3%, whereas that of bulbs immersed in distilled water was 87.5%.

What is claimed is:

1. A method of storing a plant bulb comprising the successive steps of:
    (a) immersing a plant bulb to be stored in a solution of an osmoregulator at a concentration of 5 to 10 atm for a period of from one hour to one week;
    (b) rinsing the bulb to remove the osmoregulator from it;
    (c) placing the thus-treated bulb and a moisture retainer in a sealed container; and
    (d) storing the bulb in the sealed container at room temperature.

2. The method of claim 1, in which the container is oxygen permeable.

3. The method of claim 1, in which the moisture retainer is moss, sawdust or vermiculite.

4. The method of claim 1, in which the plant bulb immersed in the osmoregulator solution in step (a) for one to three days.

5. The method of claim 1, in which the osmoregulator is selected from sucrose, glucose, fructose, mannose, sorbitol or mannitol.

6. The method of claim 1, in which the osmoregulator is sucrose.

7. The method of claim 1, in which the osmoregulator is sorbitol.

8. The method of claim 1, in which the plant bulb is a white trumpet lily.

* * * * *